United States Patent

Okawa et al.

Patent Number: 5,370,867
Date of Patent: Dec. 6, 1994

[54] BATH COMPOSITION

[75] Inventors: Wataru Okawa, Utsunomiya; Hirohisa Suzuki, Haga; Hidenori Yorozu, Utsunomiya, all of Japan

[73] Assignee: Kao Corporation, Tokyo, Japan

[21] Appl. No.: 962,723

[22] Filed: Oct. 19, 1992

[30] Foreign Application Priority Data

Oct. 17, 1991 [JP] Japan .................. 3-269501
Oct. 17, 1991 [JP] Japan .................. 3-269502

[51] Int. Cl.$^5$ .................. A61K 31/19; A61K 33/06
[52] U.S. Cl. .................. 424/78.02; 424/466; 424/601; 424/603; 424/401
[58] Field of Search .............. 424/401, 466, 601, 603, 424/78.02, 78.03, 405, 682; 128/365

[56] References Cited

U.S. PATENT DOCUMENTS

| | | | |
|---|---|---|---|
| 2,371,862 | 3/1945 | Wershaw | 424/709 |
| 3,779,932 | 12/1973 | Jaggers et al. | 252/174.11 |
| 3,817,308 | 6/1974 | Bundo | 159/48.1 |
| 3,886,125 | 5/1975 | Chromecek | 424/59 |
| 3,966,902 | 6/1976 | Chromecek | 424/59 |
| 4,181,718 | 1/1980 | Mason et al. | 424/180 |
| 4,666,707 | 5/1987 | Equchi et al. | 424/44 |
| 5,160,448 | 11/1992 | Corring | 252/174.21 |

FOREIGN PATENT DOCUMENTS

| | | |
|---|---|---|
| 0150250 | 8/1985 | European Pat. Off. |
| 0275981 | 7/1988 | European Pat. Off. |
| 0323209 | 5/1989 | European Pat. Off. |
| 0339276 | 11/1989 | European Pat. Off. |
| 1088471 | 9/1960 | Germany |
| 2158463 | 5/1973 | Germany |
| 57-102814 | 6/1982 | Japan .................. 424/466 |
| 63-258806 | 10/1988 | Japan |
| 1-294618 | 11/1989 | Japan |

OTHER PUBLICATIONS

G. A. Nowak, "Die Kosmetischen Praparate, Rezeptur, Herstellung und Wissenschaftliche Grundlage" Verlag Fur Chem. Industrie, pp. 672–674.

*Primary Examiner*—Thurman K. Page
*Assistant Examiner*—Peter F. Kulkosky
*Attorney, Agent, or Firm*—Oblon, Spivak, McClelland, Maier & Neustadt

[57] ABSTRACT

Bath compositions comprising a complex powder comprising a water-soluble polymer and a water-soluble aluminum salt; and also a bath composition which comprises a complex powder containing a water-soluble polymer, a polyphosphoric acid or a salt thereof and a water-soluble aluminum salt. Such compositions provide a refreshing and comfortable sensation of dryness to the skin; do not form water-insoluble particles, agglomerates, or flocculants; and provide an agreeable appearance and a pleasant feeling to the bath water.

17 Claims, No Drawings

BATH COMPOSITION

BACKGROUND OF THE INVENTION

1. Field of the Invention

This invention relates to a bath composition comprising a complex powder of a water-soluble polymer and a water-soluble aluminum salt which dissolve easily in bath water without producing agglomerates. Such bath compositions, when dissolved and dispersed in bath water, can simulate an alum hot spring, and provide, upon bathing, a refreshing and comfortable feeling of dryness to the skin. The present invention also pertains to a bath containing such a bath composition; and a method of bathing using such a bath composition.

2. Discussion of the Background

Aluminum sulfate and its related salts, exemplified by alum and similar salts, are known components of alum springs. These compounds suppress perspiration and provide a refreshing and comfortable feeling of dryness to the skin, as a result of their astringent property.

Recently, people have sought to enjoy the sensation of a natural hot spring in their home and various bath compositions or bath additives which contain components of natural hot springs have been developed to provide such a sensation. However, when salts of aluminum sulfate have been incorporated into a bath composition and dispersed in water to form an artificial alum spring, the salts react with other water-soluble inorganic salts contained in the bath composition to produce water-insoluble white particles or agglomerates. These agglomerates mar the appearance of the bath water. Moreover, since these agglomerates are hard particles, a disagreeable skin sensation results. If the salts of aluminum sulfates are incorporated into an effervescent bath composition containing a carbonate and a neutralizer, then water-insoluble white agglomerates of even larger size are produced. These agglomerates float on the surface of bath water because of the carbon dioxide gas generated in the agglomerates. Such bath water has a very disagreeable appearance.

Pigments are also commonly used in bath compositions. Water-insoluble pigments, such as, titanium oxide and similar pigments, make bath water opaque when, as components of a bath preparation, they are added to bath water. The opaque bath water more effectively simulates the feeling of a natural hot spring. Moreover, since titanium oxide and similar pigments are in the form of powders, they provide a comfortable dry feeling.

When salts of aluminum sulfates and water-insoluble pigments are blended in a bath composition for use in an artificial alum spring (hereinafter referred to as alum bath or alum bath water), the pigments cohere and precipitate due to the flocculating action of the water-soluble aluminum salts. This results in clear bath water. If titanium oxide or similar pigments and salts of aluminum sulfates are incorporated into an effervescent bath preparation containing a carbonate and a neutralizer, then water-insoluble white wads are produced, which float on the surface of the bath water (because of carbon dioxide gas). This gives a disagreeable appearance to the bath water. These white wads not only destroy the sensation of a hot spring, but also impart an unpleasant skin sensation.

To avoid such problems in the preparation of an opaque alum bath, the salts of aluminum sulfates must be prevented from forming water-insoluble materials in the presence of other water-soluble inorganic salts. This can be achieved by making the pH of the bath water either strongly acidic, with a pH not higher than 4, or strongly basic, with a pH not lower than 10.5. However, such strongly acidic or strongly basic bath water injures the skin and damages the bath tub and heating device.

Therefore, there remains a need for a bath composition which dissolves and disperses easily into bath water and provides an alum bath which does not damage skin, tub or heating device.

SUMMARY OF THE INVENTION

Accordingly, it is an object of the present invention, to provide a novel complex powder comprising a water-soluble polymer and a water-soluble aluminum salt.

It is another object of the present invention to provide a bath composition comprising a complex powder (a), which comprises a water-soluble polymer and a water-soluble aluminum salt.

It is another object of the present invention to provide a complex powder comprising a water-soluble polymer, a polyphosphoric acid or a salt thereof, and a water-soluble aluminum salt.

It is another object of the present invention to provide a bath composition comprising a complex powder (b), which comprises a water-soluble polymer, a polyphosphoric acid or a salt thereof, and a water-soluble aluminum salt.

It is another object of the present invention to provide a bath composition comprising a pigment, a polyphosphoric acid or a salt thereof and a complex powder (a), which comprises a water-soluble polymer and a water-soluble aluminum salt.

It is another object of the present invention to provide a bath composition comprising a pigment and a complex powder (b), which comprises a water-soluble polymer, a polyphosphoric acid or a salt thereof and a water-soluble aluminum salt.

It is another object of the present invention to provide a bath containing such a bath composition.

It is another object of the present invention to provide a method of bathing utilizing such a bath composition.

A more complete appreciation of the invention and many of the attendant advantages thereof will be readily obtained as the same become better understood by reference to the following description.

DETAILED DESCRIPTION OF THE INVENTION AND PREFERRED EMBODIMENTS

The complex powder (a) comprising a water-soluble polymer and a water-soluble aluminum salt is prepared by heating and dissolving the water-soluble polymer either with or without a small amount of water, to which the water-soluble aluminum salt is added and mixed under heat, followed by cooling and pulverizing.

Preferred examples of the water-soluble polymer include polyethylene glycol (PEG), polyvinyl alcohol (PVA), carboxymethylcellulose (CMC), polyvinyl pyrrolidone (PVP), hydroxypropylcellulose (HPC), acacia, gelatin, carrageenan and sodium alginate. These water-soluble polymers can be used singly or as a mixture of two or more. The preferable amount is 0.1 to 20 times, especially 1 to 10 times by weight relative to the weight of the aluminum salts.

The water-soluble aluminum salts useful in this invention are not limited and preferred examples are aluminum sulfate, aluminum potassium sulfate, aluminum sodium sulfate, ammonium alum, aluminum phosphate, aluminum chloride, aluminum acetate, aluminum di-dl-pyrrolidone-carboxylate, aluminum benzoate, aluminum citrate, aluminum nitrate, chlorohydroxy aluminum, aluminum oxalate, aluminum lactate and the like, among which aluminum sulfate, aluminum potassium sulfate, aluminum sodium sulfate and other aluminum sulfate salts are especially preferred.

The complex powder (b) comprising a water-soluble polymer, a polyphosphoric acid or a salt thereof, and a water-soluble aluminum salt is prepared by heating and melting a water-soluble polymer with or without a small amount of water, to which the water-soluble aluminum salt and a polyphosphoric acid or a salt thereof are added and mixed under heat, followed by cooling and pulverizing.

The salts of polyphosphoric acid are not limited and may be either linear or cyclic. Preferred examples include sodium metaphosphate, potassium metaphosphate, sodium polyphosphate, potassium polyphosphate, sodium tripolyphosphate, potassium tripolyphosphate and the like. They can be used singly or in combination. The amount of polyphosphoric acid or its salts employed is 0.5 to 10 times by weight relative to the weight of the water-soluble aluminum salt.

The water-soluble polymers and water-soluble aluminum salts which are useful for preparing complex powder (b) are those mentioned above and the amounts are the same as described in the production of complex powder (a).

Both complex powders (a) and (b) dissolve well in bath water and are suitable in bath compositions. These ingredients can be used singly or in combination, and the amounts are 0.1 to 20% by weight of the water-soluble aluminum salt relative to the total weight of the bath composition.

A bath composition which is capable of providing an excellent opaque alum bath can be prepared by blending the complex powders (a) and (b) and pigment (d).

The pigments are not limited and preferred examples include titanium oxide, kaolin, talc, titanated mica, mica, yellow iron oxide, carbon black, black iron oxide, zinc oxide, magnesium oxide, polyethylene powder, silicone powder and barium sulfate. These pigments can be used singly or in combination and are used in amounts of 0.01 to 10% by weight relative to the total weight of the bath composition.

Bath compositions comprising complex powder (b) and a pigment are particularly excellent in dispersing the pigment. On the other hand, bath compositions comprising complex powder (a) and a pigment preferably further contain a polyphosphoric acid or a salt thereof. In this case, the amount of the polyphosphoric acid or a salt thereof employed is preferably in a range of 0.5 to 10 times by weight relative to the amount of the water-soluble aluminum salt. The polyphosphoric acid or a salt thereof used for this purpose is the same as employed in the manufacture of complex powder (b).

The bath compositions of the present invention may further comprise other optional ingredients which are ordinarily incorporated as bath additives. Examples of the optional ingredients include sodium bicarbonate, sodium carbonate, Glauber's salt, sulfur, atractylodes root, atractylodes macrocephala, sodium chloride, Japanese valerian, cnidium, bitter orange peel, ligusticum, dl-menthol, 1-menthol, Japanese peppermint oil, hot spring deposits, colorants, glycerol, potassium sulfide, sodium sulfide, jasmine, calcium oxide, ethanol, d-camphor, dl-camphor, ginger root powder, potassium nitrate, sodium nitrate, calcium nitrate, iron subsulfide, metasilicic acid, casein, silicic acid anhydride, neutral terra abla, Ginseng, cassia bark, peony, Japanese peppermint, tuckahoe, calamus root, angelica root, Houttuynia cordata, white cedar oil, bitter orange peel oil, methyl salicylate, borneol, sodium thiosulfate, turpentine oil, potassium soap, calcium hydrogen phosphate, stearyl alcohol, sodium salicylate, potassium bromide, potassium chloride, ammonium chloride, iron sulfate, slaked lime, cinnamon oil, bergamot oil, calamus oil, pine oil, lavender oil, rice-bran oil, rice-bran extract, olive oil, soybean oil, liquid paraffin, white petrolatum, propylene glycol, artificial Carlsbad mineral salt, saffron, phellondendron extract, dextrin, potassium permanganate, sodium phosphate, fennel, dried orange peel, yolk powder, citri pericarpium pulveratum, sodium hyposulfite, calcium thiosulfate, sodium hydroxide, mica powder, German chamomile, and powdered skim milk.

For preparing effervescent bathing preparations, carbonates, such as, sodium sesquicarbonate, magnesium bicarbonate, magnesium carbonate, potassium carbonate, calcium carbonate and similar carbonate salts can be incorporated as effervescent ingredients, and solid and water-soluble acids, such as succinic acid, adipic acid, malic acid, tartaric acid, malonic acid, pyrrolidone carboxylic acid, phosphoric acid, amino acid, fumaric acid and similar acids can be used as neutralizers.

The bath compositions of the present invention are prepared by mixing the above-mentioned components to form powders, granules, or tablets all by conventional methods.

Those bath compositions of the present invention, which do not contain pigments provide the skin with a refreshing and comfortable sensation of dryness. Moreover, since water-insoluble white particles or agglomerates are not produced, the resultant alum bath has the agreeable appearance and pleasant sensation of bath water. Additionally, there is no damage to the bath tub or heating device.

Those bath compositions of the present invention which contain pigments also provide the skin with a refreshing and comfortable sensation of dryness. Moreover, since flocculations and precipitations are not produced, beautifully opaque bath water can be obtained. There is also no damage to the bath tub or heating devices.

In another embodiment, the present invention relates to a bath which contains the present bath composition. Thus, the present invention relates to a bath comprising water and a bath composition comprising a complex powder comprising a water-soluble polymer and a water-soluble aluminum salt. In a preferred embodiment, the present bath further comprises a polyphosphoric acid or a salt thereof. In another preferred embodiment, the present bath further comprises a polyphosphoric acid or a salt thereof and a pigment. Of course, the present bath may further comprise one or more of the above-described bath additives in the conventional amount.

Typically, the present bath will be of sufficient volume for immersion of a part of the body from the smallest in extremity, such as a hand or foot, to as large as a whole body, preferably excluding the head. Thus, the bath will suitably have a volume of 1 to 300 liters, preferably 100 to 200 liters.

The present bath may be prepared by dissolving the present bath composition in a sufficient amount of water. It is preferred that the concentration of a water-soluble aluminum salt in the bath water be from 0.05 to 100 ppm, preferably 0.1 to 40 ppm upon bathing.

In another embodiment, the present invention relates to a method of bathing comprising immersing a part of a human body in the present bath containing a water-soluble aluminum salt in such an amount to provide a concentration of from 0.05 to 100 ppm, preferably 0.1 to 40 ppm upon bathing. As noted above, the part of the human to be immersed may be as small as an extremity, such as a hand or foot, to as large as a whole body, preferably excluding the head. Suitably, the immersion is carried out for a time of 1 minute to 2 hours, preferably 5 minutes to 1 hour. For best results, the temperature of the bath should be in a range of 35° to 45° C., preferably about 40° C. at the beginning of the immersion. In the usual procedure utilizing a conventional bath tub without a heat source, the bath temperature will gradually decrease during the immersion. However, the present invention may be practiced with a bathtub which is equipped with a heating device so that the preferred temperature of the bath may be maintained throughout the immersion.

Other features of the invention will become apparent in the course of the following descriptions of exemplary embodiments which are given for illustration of the invention and are not intended to be limiting thereof.

EXAMPLES

Example 1

Preparation of a complex powder containing alum:

600 g of polyethylene glycol (weight average molecular weight: 6000, PEG 6000) was placed in a 1-liter table kneader equipped with a heating jacket, and heated and melted, while 80° C. water circulated in the jacket. 200 g of alum was added to the kneader and mixed under heat for 20 minutes. Thereafter, cold water (room temperature) was circulated while mixing was continued to perform a cold mixing of the melted product. The obtained cold material was pulverized with a mixer to obtain an alum-treated powder having a particle size which passes through a 710 micro meter mesh.

Example 2

Preparation of a complex powder containing aluminum sulfate:

500 g of polyethylene glycol (PEG 6000) was placed in a 1-liter table kneader equipped with a heating jacket, and heated and melted while 80° C. water circulated in the jacket. 100 g of aluminum sulfate was added to the kneader, and mixing was performed under heat for 20 minutes. Thereafter, while mixing was continued, cold water (room temperature) was circulated to perform a cold mixing of the melted product. The obtained cold material was pulverized with a mixer to obtain an aluminum sulfate-treated powder having a particle size which passes through a 710 micro meter mesh.

Example 3

Preparation of a complex powder containing aluminum sulfate and metaphosphate:

400 g of polyethylene glycol (PEG 6000) was placed in a 1-liter table kneader equipped with a heating jacket, and heated and melted, while 80° C. water circulated in the jacket. 100 g of aluminum sulfate and 500 g of sodium metaphosphate were added to the kneader, and mixing was performed under heat for 30 minutes. Thereafter, while mixing was continued, cold water (room temperature) was circulated to perform a cold mixing of the melted product. The obtained cold material was pulverized with a mixer to obtain a powder containing aluminum sulfate and metaphosphate having a particle size which passes through a 710 micro meter mesh.

Comparison 1

The bath compositions of Table 1 were employed to prepare alum baths and an expert panel evaluated the dissolvability of the bath compositions and the skin sensations experienced during and after bathing. The results are shown in Table 1.

For each bath 50 g of a bath composition were added to 180 liters of bath water, which is equivalent to 3 g of alum or aluminum sulfate per bath.

TABLE 1

| Ingredients | Invention product 1 (powder) porportion | Comparative product 1 (powder) proportion | Invention product 2 (tablet) proportion | (% by weight) Comparative product 2 (tablet) proportion |
| --- | --- | --- | --- | --- |
| Sodium bicarbonate | 25 | 25 | 22 | 22 |
| Sodium carbonate | — | — | 12 | 12 |
| Succinic acid | — | — | 20 | 20 |
| Fumaric acid | — | — | 9 | 9 |
| Sodium sulfate | 46 | 46 | — | — |
| PEG6000 | — | 18 | — | 30 |
| Dextrin | 5 | 5 | 1 | 1 |
| Purfume, Colorant | trace | trace | trace | trace |
| Alum-containing complex powder of Ex. 1 | 24 | — | — | — |
| Aluminum sulfate-containing complex powder of Ex. 2 | — | — | 36 | — |
| Alum | — | 6 | — | 6 |
| Total | 100.0 | 100.0 | 100.0 | 100.0 |
| Observation of bath water | | | | |
| White agglomerates | none | produced | none | produced |
| Flocculations on the surface of bath water | — | — | none | produced |
| Dissolvability | good | not good | good | not good |

TABLE 1-continued

| Ingredients | Invention product 1 (powder) porportion | Comparative product 1 (powder) proportion | Invention product 2 (tablet) proportion | (% by weight) Comparative product 2 (tablet) proportion |
| --- | --- | --- | --- | --- |
| Skin sensation during bathing | good | not good | good | not good |
| Skin sensation after bathing | good | not good | good | not good |
| pH when dissolved in bath water | 7.0 | 7.0 | 6.2 | 6.2 |

As demonstrated in Table 1, Invention Products 1 and 2, which correspond to the complex powders of the present invention, exhibited excellent dissolvability and provided a refreshing and comfortable sensation of dryness to the skin during and after the bath.

In contrast, Comparative Products 1 and 2 produced white agglomerates, did not dissolve well, resulted in flocculation (for Comparative Product 2), and did not provide a pleasant sensation during and after bathing.

Comparison 2

The bath compositions of Table 2 were employed to prepare alum baths, and an expert panel evaluated agglomeration, dissolvability, the state of bath water (flocculation/precipitation) on the following day, and skin sensations experienced during and after bathing. The results are shown in Table 2.

For each bath, 50 g of a bath composition were added to 180 liter of bath water, which is equivalent to 2.5 g of titanium oxide as a turbidity agent per bath and 3 g of alum or aluminum sulfate as a water-soluble aluminum salt per bath.

As shown in Table 2, Invention Products 3 and 4, which correspond to the complex powders of the present invention, did not produce agglomeration and exhibited excellent dissolvability and dispersibility on the following day. Further, they provided a refreshing and comfortable sensation of dryness to the skin during and after the bath.

In contrast, Comparative Products 3 and 4 produced white agglomerates, did not dissolve well, exhibited flocculation or precipitation on the following day, and did not provide a pleasant sensation during or after bathing.

As is clearly understood from Tables 1 and 2, the bath compositions of the present invention do not produce agglomeration, exhibit excellent dissolvability and dispersibility, and provide a refreshing and comfortable sensation of dryness to the skin during and after the bath.

Obviously, numerous modifications and variations of the present invention are possible in light of the above teachings. It is therefore to be understood that, within the scope of the appended claims, the invention may be practiced otherwise than as specifically described herein.

What is claimed is:

1. A complex powder consisting essentially of a water-soluble polymer, a polyphosphoric acid or a salt thereof and a water-soluble aluminum salt, wherein
   said water-soluble polymer is present in an amount of 0.1 to 20 times by weight relative to the weight of the water-soluble aluminum salt, and
   said polyphosphoric acid or a salt thereof is present in an amount of 0.5 to 10 times by weight relative to the weight of the water-soluble aluminum salt,
   said complex powder in a bath composition not agglomerating exhibiting good dissolvability and disperability, and providing refreshing and comfortable sensation of dryness to the skin during and after a bath.

TABLE 2

| Ingredients | Invention product 3 (powder) porportion | Comparative product 3 (powder) proportion | Invention product 4 (tablet) proportion | (% by weight) Comparative product 4 (tablet) proportion |
| --- | --- | --- | --- | --- |
| Sodium bicarbonate | 25 | 25 | 10 | 10 |
| Sodium carbonate | — | — | 10 | 10 |
| Succinic acid | — | — | 10 | 10 |
| Fumaric acid | — | — | 4 | 4 |
| Sodium sulfate | 26 | 41 | — | — |
| PEG6000 | — | 18 | — | 54 |
| Dextrin | 5 | 5 | 1 | 1 |
| Purfume, Colorant | trace | trace | trace | trace |
| Titanium oxide | 5 | 5 | 5 | 5 |
| Sodium metaphosphate | 15 | — | — | — |
| Alum-containing complex powder of Ex. 1 | 24 | — | — | — |
| Aluminum sulfate.metaphosphate complex powder of Ex. 3 | — | — | 60*) | — |
| Alum | — | — | — | 6 |
| Total | 100.0 | 100.0 | 100.0 | 100.0 |
| Observation of bath water | | | | |
| White agglomerates | none | produced | none | produced |
| Dissolvability | good | not good | good | not good |
| Flocculation/precipitation on the following day | none | observed | none | observed |
| Skin sensation during/after bathing | good | not good | good | not good |
| pH when dissolved in bath water | 7.2 | 7.0 | 6.3 | 6.1 |

*)20% by weight out of 60% by weight is sodium metaphosphate.

2. A bath composition comprising a complex powder which consists essentially of a water-soluble polymer, a polyphosphoric acid or a salt thereof and a water-soluble aluminum salt, wherein said water-soluble polymer is present in an amount of 0.1 to 20 times by weight relative to the weight of the water-soluble aluminum salt, and said polyphosphoric acid or a salt thereof is present in an amount of 0.5 to 10 times by weight relative to the weight of the water-soluble aluminum salt, said complex powder in said bath composition not agglomerating, exhibiting good dissolvability and disperability, and providing refreshing and comfortable sensation of dryness to the skin during and after a bath.

3. The both composition of claim 2, wherein said water-soluble aluminum salt is a salt of aluminum sulfate.

4. A bath composition comprising a pigment and a complex powder which complex powder consists essentially of a water-soluble polymer, a polyphosphoric acid or a salt thereof and a water-soluble aluminum salt, wherein said water-soluble polymer is present in an amount of 0.1 to 20 times by weight relative to the weight of the water-soluble aluminum salt, said polyphosphoric acid or a salt thereof is present in an amount of 0.5 to 10 times by weight relative to the weight of the water-soluble aluminum salt, and said pigment is present in an amount of 0.01 to 10% by weight relative to the total weight of the bath compositional said complex powder in said bath composition not agglomerating, exhibiting good dissolvability and disperability, and providing refreshing and comfortable sensation of dryness to the skin during and after a bath.

5. The bath composition of claim 4, wherein said water-soluble aluminum salt is a salt of aluminum sulfate.

6. A bath, comprising water and a bath composition, which bath composition comprises a complex powder, which complex powder consists essentially of a water-soluble polymer, a polyphosphoric acid or a salt thereof and a water-soluble aluminum salt, wherein said water-soluble polymer is present in an amount of 0.1 to 20 times by weight relative to the weight of the water-soluble aluminum salt, and said polyphosphoric acid or a salt thereof is present in an amount of 0.5 to 10 times by weight relative to the weight of the water-soluble aluminum salt, said complex powder in said bath composition not agglomerating, exhibiting good dissolvability and disperability, and providing refreshing and comfortable sensation of dryness to the skin during and after a bath.

7. The both of claim 6, wherein said water-soluble aluminum salt is a salt of aluminum sulfate.

8. A bath, comprising water and a bath composition, which bath composition comprises a pigment and a complex powder which complex powder consists essentially of a water-soluble polymer, a polyphosphoric acid or a salt thereof and a water-soluble aluminum salt, wherein said water-soluble polymer is present in an amount of 0.1 to 20 times by weight relative to the weight of the water-soluble aluminum salt, and said polyphosphoric acid or a salt thereof is present in an amount of 0.5 to 10 times by weight relative to the weight of the water-soluble aluminum salt, said complex powder in said bath composition not agglomerating, exhibiting good dissolvability and disperability, and providing refreshing and comfortable sensation of dryness to the skin during and after a bath.

9. A method of bathing, comprising immersing a part of the human body in a bath comprising a bath composition and water, wherein said bath composition comprises a complex powder, which complex powder consists essentially of a water-soluble polymer, a polyphosphoric acid or a salt thereof and a water-soluble aluminum salt, wherein said water-soluble polymer is present in an amount of 0.1 to 20 times by weight relative to the weight of the water-soluble aluminum salt, and said polyphosphoric acid or a salt thereof is present in an amount of 0.5 to 10 times by weight relative to the weight of the water-soluble aluminum salt.

said complex powder in said bath composition not agglomerating, exhibiting good dissolvability and disperability, and providing refreshing and comfortable sensation of dryness to the skin during and after a bath.

10. A method of bathing, comprising immersing a part of the human body in a bath comprising a bath composition and water, wherein said bath composition comprises a pigment and a complex powder which complex powder consists essentially of a water-soluble polymer, a polyphosphoric acid or a salt thereof and a water-soluble aluminum salt, wherein said water-soluble polymer is present in an amount of 0.1 to 20 times by weight relative to the weight of the water-soluble aluminum salt, said polyphosphoric acid or a salt thereof is present in an amount of 0.5 to 10 times by weight relative to the weight of the water-soluble aluminum salt, and said pigment is present in an amount of 0.01 to 10% by weight relative to the total weight of the bath composition, said complex powder in said bath composition not agglomerating, exhibiting good dissolvability and disperability, and providing refreshing and comfortable sensation of dryness to the skin during and after a bath.

11. The complex powder of claim 1, wherein said complex powder is prepared by heating and melting a water-soluble polymer with or without a small amount of water, to which the water-soluble aluminum salt and polyphosphoric acid or a salt thereof are added and mixed under heat, followed by cooling and pulverizing.

12. The bath composition of claim 2, wherein said complex powder is prepared by heating and melting the water-soluble polymer with or without a small amount of water, to which the water-soluble aluminum salt and polyphosphoric acid or a salt thereof are added and mixed under heat, followed by cooling and pulverizing.

13. The bath composition of claim 4, wherein said complex powder is prepared by heating and melting the water-soluble polymer with or without a small amount of water, to which the water-soluble aluminum salt and polyphosphoric acid or a salt thereof are added and mixed under heat, followed by cooling and pulverizing.

14. The bath composition of claim 6, wherein said complex powder is prepared by heating and melting the water-soluble polymer with or without a small amount of water, to which the water-soluble aluminum salt and polyphosphoric acid or a salt thereof are added and mixed under heat, followed by cooling and pulverizing.

15. The bath composition of claim 8, wherein said complex powder is prepared by heating and melting the water-soluble polymer with or without a small amount of water, to which the water-soluble aluminum salt and polyphosphoric acid or a salt thereof are added and mixed under heat, followed by cooling and pulverizing.

16. The method of bathing of claim 9, wherein said complex powder is prepared by heating and melting the water-soluble polymer with or without a small amount of water, to which the water-soluble aluminum salt and polyphosphoric acid or a salt thereof are added and mixed under heat, followed by cooling and pulverizing 17. The method of bathing of claim 10, wherein said complex powder is prepared by heating and melting the water-soluble polymer with or without a small amount of water, to which the water-soluble aluminum salt and polyphosphoric acid or a salt thereof are added and mixed under heat, followed by cooling and pulverizing.

* * * * *